US011608596B2

(12) United States Patent
Pande et al.

(10) Patent No.: US 11,608,596 B2
(45) Date of Patent: Mar. 21, 2023

(54) PAPER PRODUCTS SUBJECTED TO A SURFACE TREATMENT COMPRISING ENZYME-TREATED SURFACE ENHANCED PULP FIBERS AND METHODS OF MAKING THE SAME

(71) Applicants: DOMTAR PAPER COMPANY, LLC, Fort Mill, SC (US); THE UNIVERSITY OF BRITISH COLUMBIA, Vancouver (CA)

(72) Inventors: Harshad Pande, Fort Mill, SC (US); Alexander Timothy Beam, Fort Mill, SC (US); Mark Martinez, Vancouver (CA); Jingqian Chen, Vancouver (CA); Miaoran Li, Vancouver (CA); Heather Trajano, Vancouver (CA)

(73) Assignees: Domtar Paper Company, LLC, Fort Mill, SC (US); The University of British Columbia, Vancouver (CA)

( * ) Notice: Subject to any disclaimer, the term of this patent is extended or adjusted under 35 U.S.C. 154(b) by 385 days.

(21) Appl. No.: 16/831,582

(22) Filed: Mar. 26, 2020

(65) Prior Publication Data
US 2020/0308769 A1 Oct. 1, 2020

Related U.S. Application Data

(60) Provisional application No. 62/824,113, filed on Mar. 26, 2019.

(51) Int. Cl.
*D21H 11/20* (2006.01)
*D21H 21/16* (2006.01)
(Continued)

(52) U.S. Cl.
CPC ........... *D21H 11/20* (2013.01); *C12N 9/2405* (2013.01); *D21H 19/54* (2013.01); *C12Y 302/01091* (2013.01); *D21H 21/16* (2013.01)

(58) Field of Classification Search
None
See application file for complete search history.

(56) References Cited

U.S. PATENT DOCUMENTS 3,098,785 A 7/1963 Meiler
3,388,037 A 6/1968 Asplund et al.
(Continued)

FOREIGN PATENT DOCUMENTS

AU 2013305802 8/2012
AU 2015218812 8/2015
(Continued)

OTHER PUBLICATIONS

Smook, Gary A., Handbook for Pulp and Paper Technologists, 2nd ed, Angus Wilde Publications, 1992, p. 228. (Year: 1992).*
(Continued)

*Primary Examiner* — Dennis R Cordray
(74) *Attorney, Agent, or Firm* — Troutman Pepper Hamilton Sanders LLP (57) ABSTRACT

Methods of making a paper product can comprise forming a substrate from a first furnish that comprises a plurality of pulp fibers, at least partially dewatering the substrate, treating a second furnish that comprises a plurality of surface enhanced pulp fibers (SEPF) at least by adding one or more enzymes to the second furnish, and sizing the dewatered substrate at least by depositing the treated second furnish onto at least one of opposing first and second surfaces of the dewatered substrate. The SEPF can have a length weighted average fiber length that is greater than or equal to 0.20 millimeters (mm) and an average hydrodynamic specific
(Continued)

surface area that is greater than or equal to 10 square meters per gram (m²/g).

17 Claims, 9 Drawing Sheets

(51) Int. Cl.
*D21H 19/54* (2006.01)
*C12N 9/24* (2006.01)

(56) References Cited

U.S. PATENT DOCUMENTS

| | | | |
|---|---|---|---|
| 3,708,130 A | 1/1973 | Perry | |
| 3,794,558 A | 2/1974 | Back | |
| 3,891,499 A | 6/1975 | Kato et al. | |
| 3,920,508 A | 11/1975 | Yonemori | |
| 3,966,543 A | 6/1976 | Cayle et al. | |
| 4,012,279 A | 3/1977 | Selander et al. | |
| 4,054,625 A | 10/1977 | Kozlowski et al. | |
| 4,247,362 A | 1/1981 | Williams | |
| 4,635,864 A | 1/1987 | Peterson et al. | |
| 4,895,019 A | 1/1990 | Lehmikangas et al. | |
| 5,110,412 A | 5/1992 | Fuentes et al. | |
| 5,248,099 A | 9/1993 | Lahner et al. | |
| 5,308,449 A | 5/1994 | Fuentes et al. | |
| 5,695,136 A | 12/1997 | Rohden et al. | |
| 5,731,080 A | 3/1998 | Cousin et al. | |
| 5,824,364 A | 10/1998 | Cousin et al. | |
| 5,954,283 A | 9/1999 | Matthew | |
| 6,156,118 A | 12/2000 | Silenius | |
| 6,165,317 A | 12/2000 | Sabourin | |
| 6,251,222 B1 | 6/2001 | Silenius et al. | |
| 6,296,736 B1 | 10/2001 | Hsu et al. | |
| 6,375,974 B1 | 4/2002 | Ito et al. | |
| 6,599,391 B2 | 7/2003 | Silenius et al. | |
| 6,773,552 B1 | 8/2004 | Albert et al. | |
| 6,861,380 B2 | 3/2005 | Garnier et al. | |
| 6,887,350 B2 | 5/2005 | Garnier et al. | |
| 6,935,589 B1 | 8/2005 | Matthew | |
| 6,946,058 B2 | 9/2005 | Hu | |
| 6,955,309 B2 | 10/2005 | Matthew et al. | |
| 7,381,294 B2 | 6/2008 | Suzuki et al. | |
| 7,624,879 B2 | 12/2009 | Frances | |
| 7,741,234 B2 | 6/2010 | Smith et al. | |
| 7,942,964 B2 | 5/2011 | Luo et al. | |
| 8,871,057 B2 | 10/2014 | Gane et al. | |
| 9,879,361 B2 | 1/2018 | Pande et al. | |
| 9,920,484 B2 | 3/2018 | Marcoccia et al. | |
| 9,988,762 B2 | 6/2018 | Bilodeau et al. | |
| 10,563,356 B2 | 2/2020 | Marcoccia et al. | |
| 10,704,165 B2 | 7/2020 | Pande et al. | |
| 10,710,930 B2 | 7/2020 | Marcoccia et al. | |
| 2002/0059886 A1 | 5/2002 | Merkley et al. | |
| 2002/0069791 A1 | 6/2002 | Merkley et al. | |
| 2002/0084046 A1 | 7/2002 | Hsu et al. | |
| 2003/0111197 A1 | 6/2003 | Hu | |
| 2004/0112558 A1 | 6/2004 | Garnier et al. | |
| 2004/0112997 A1 | 6/2004 | Matthew et al. | |
| 2004/0180184 A1 | 9/2004 | Fillion et al. | |
| 2004/0241350 A1 | 12/2004 | Koga et al. | |
| 2005/0194477 A1 | 9/2005 | Suzuki | |
| 2006/0006264 A1 | 1/2006 | Sabourin et al. | |
| 2007/0164143 A1 | 7/2007 | Sabourin et al. | |
| 2008/0148999 A1 | 6/2008 | Luo et al. | |
| 2008/0227161 A1 | 9/2008 | Levie et al. | |
| 2009/0145562 A1 | 6/2009 | Nguyen | |
| 2009/0145842 A1 | 6/2009 | Frances | |
| 2009/0162602 A1 | 6/2009 | Cottier et al. | |
| 2009/0221812 A1 | 9/2009 | Ankerfors et al. | |
| 2009/0266500 A1 | 10/2009 | Schubert et al. | |
| 2010/0065236 A1 | 3/2010 | Henriksson et al. | |
| 2010/0218908 A1 | 9/2010 | Silenius et al. | |
| 2010/0288456 A1 | 11/2010 | Westland et al. | |
| 2011/0277947 A1 | 11/2011 | Hua et al. | |
| 2011/0314726 A1 | 12/2011 | Jameel et al. | |
| 2012/0007363 A1 | 1/2012 | Wang | |
| 2012/0012031 A1 | 1/2012 | Husband et al. | |
| 2013/0202870 A1 | 8/2013 | Malmborg et al. | |
| 2014/0057105 A1 | 2/2014 | Pande et al. | |
| 2014/0116635 A1 | 5/2014 | Porto et al. | |
| 2014/0180184 A1 | 6/2014 | Duguid | |
| 2014/0209260 A1 | 7/2014 | Li et al. | |
| 2014/0209264 A1 | 7/2014 | Tirimacco et al. | |
| 2014/0302117 A1 | 10/2014 | Moen et al. | |
| 2015/0299955 A1 | 10/2015 | Laukkanen et al. | |
| 2016/0333524 A1 | 11/2016 | Pande et al. | |
| 2016/0340802 A1 | 11/2016 | Pande et al. | |
| 2017/0058457 A1 | 3/2017 | Marcoccia et al. | |
| 2017/0073893 A1 | 3/2017 | Bilodeau et al. | |
| 2017/0226009 A1 | 8/2017 | Marcoccia et al. | |
| 2018/0105986 A1 | 4/2018 | Harshad et al. | |
| 2018/0148895 A1 | 5/2018 | Marcoccia et al. | |
| 2019/0218716 A1 | 7/2019 | Hoglund et al. | |
| 2019/0242062 A1 | 8/2019 | Harshad et al. | |
| 2020/0063353 A1 | 2/2020 | Everett et al. | |
| 2020/0308769 A1 | 10/2020 | Pande et al. | |
| 2020/0325629 A1 | 10/2020 | Marcoccia et al. | |
| 2020/0340155 A1 | 10/2020 | Pande et al. | |

FOREIGN PATENT DOCUMENTS

| | | |
|---|---|---|
| CA | 2883161 | 2/2014 |
| CN | 1516768 | 7/2004 |
| CN | 1718914 | 1/2006 |
| CN | 101691700 | 4/2010 |
| CN | 102971462 | 3/2013 |
| CN | 103590283 | 2/2014 |
| EP | 0333209 | 9/1989 |
| EP | 0333212 | 9/1989 |
| EP | 2220291 | 5/2017 |
| FR | 2520769 | 8/1983 |
| JP | S58-136895 | 8/1983 |
| JP | H02229747 | 9/1990 |
| JP | H03122038 | 5/1991 |
| JP | H04194097 | 7/1992 |
| JP | H 04263699 | 9/1992 |
| JP | H07165456 | 6/1995 |
| JP | H08197836 | 8/1996 |
| JP | H08284090 | 10/1996 |
| JP | H09124950 | 5/1997 |
| JP | 2002194691 | 7/2002 |
| JP | 2004525284 | 8/2004 |
| JP | 2004360088 | 12/2004 |
| JP | 2007231438 | 9/2007 |
| JP | 2010125694 | 6/2010 |
| JP | 2012526923 | 11/2012 |
| JP | 2015526608 | 9/2015 |
| JP | 2018135631 | 8/2018 |
| KR | 2004/0022874 | 3/2004 |
| KR | 1020050086850 | 8/2005 |
| KR | 10-0662043 B | 12/2006 |
| KR | 10-2010-0090745 | 8/2010 |
| KR | 1020130132381 | 12/2013 |
| RU | 2224060 | 2/2004 |
| RU | 2309211 | 10/2007 |
| RU | 2358055 | 6/2009 |
| WO | WO 1996/004424 | 2/1996 |
| WO | WO 1998/023814 | 6/1998 |
| WO | WO 2002/014606 | 2/2002 |
| WO | WO 0214606 | 2/2002 |
| WO | WO 2002/095129 | 11/2002 |
| WO | WO 2004/101889 | 11/2004 |
| WO | WO 2009/038730 | 3/2009 |
| WO | WO 2009/155541 | 12/2009 |
| WO | WO 2010/134868 | 11/2010 |
| WO | WO 2012/007363 | 1/2012 |
| WO | WO 2012/101331 | 8/2012 |
| WO | WO 2014/031737 | 2/2014 |
| WO | WO 2014/106684 | 7/2014 |
| WO | WO 2015/127233 | 8/2015 |
| WO | WO 2015/127239 | 8/2015 |

(56) References Cited

FOREIGN PATENT DOCUMENTS

| WO | WO 2018/026804 | 2/2018 |
|----|----------------|--------|
| WO | WO 2018/051275 | 3/2018 |
| WO | WO 2019/152969 | 8/2019 |

OTHER PUBLICATIONS

Extended European Search report issued in European Patent Application No. 17195921.6, dated Nov. 20, 2017.
International Preliminary Report on Patentability issued in International Patent Application No. PCT/US2013/055971, dated Feb. 24, 2015.
International Preliminary Report on Patentability issued in International Patent Application No. PCT/US2015/016858, dated Aug. 23, 2016.
International Preliminary Report on Patentability issued in International Patent Application No. PCT/US2015/016865, dated Aug. 23, 2016.
International Search Report and Written Opinion issued in International Patent Application No. PCT/US2019/016590, dated May 23, 2019.
International Search Report and Written Opinion issued in International Patent Application No. PCT/US2013/055971, dated Oct. 14, 2013.
International Search Report and Written Opinion issued in International Patent Application No. PCT/US2015/016858, dated May 15, 2015.
International Search Report and Written Opinion issued in International Patent Application No. PCT/US2015/016865, dated May 20, 2015.
International Search Report and Written Opinion issued in International Patent Application No. PCT/US2017/057161, dated Dec. 22, 2017.
International Search Report and Written Opinion issued in International Patent Application No. PCT/US2017/044881, dated Oct. 18, 2017.
Office Action Issued in Corresponding Korean Patent Application No. 10-2015-7006955, dated May 29, 2020.
Brazilian Search Report Issued in Corresponding Brazilian Patent Application No. BR112015003819-0, dated Sep. 9, 2019.
Declaration of Harshad Pande and Bruno Marcoccia, filed in U.S. Appl. No. 13/836,760, dated Oct. 12, 2016.
Demuner et al., "Ultra low intensity refining of eucalyptus pulps." Scientific and technical advances in refining and mechanical pulping 2005.
Handbook of Pulping and Papermaking, C. Biermann, Academic Press; 2nd Edition (Aug. 5, 1996), p. 145.
Joy et al., "Ultra-Low intensity refining of short fibered pulps." African Pulp and Paper Week 2004 retrieved from URL:<https://www.tappsa.eo.za/archive2/APPW_2004/Title2004/Ultralow_intensity_refining/ultra-low_intensity_refining.html.
La Vrykova-Marrain et al., "Characterizing the drainage resistance of pulp and microfibrillar suspensions using hydrodynamic flow measurements," TAPPI's PaperCon 2012 Conference.
Pal et al., "A Simple Method for Calculation of the Permeability Coefficient of Porous Media," TAPPI Journal, 5(9):10-16, (2006).
Pala et al., "Refining and enzymatic treatment of secondary fibres for paperboard production: Cyberflex measurements of fibre flexibility" Cost E20—Wood Fibre Cell Wall Structure 2001, 4 pages.
Teixeira, "Recycled Old Corrugated Container Fibers for Wood-Fiber Cement Sheets," International Scholarly Research Network 2012(923413): 1-8, 2012.
Tonoli et al., "Effect of Fibre morphology on flocculation of fibre-cement suspensions," Cement and Concrete Research, 39:1017-1022, (2009).
U.S. Provisional Application entitled: Surface Enhanced Pulp Fibers at the Substrate Surface: Solutions, Methods of Application and Enhanced Properties, U.S. Appl. No. 61/942,694, filed Feb. 21, 2014.
U.S. Provisional Application entitled: Improved Composition of Lignin and Surface-Enhanced Pulp Fiber, U.S. Appl. No. 62/189,569, filed Jul. 7, 2015.
U.S. Provisional Application entitled: Surface Enhanced Pulp Fibers in Fiber Cement, U.S. Appl. No. 61/942,708, filed Feb. 21, 2014.
U.S. Provisional Application entitled: Surface Enhanced Pulp Fibers, Methods of Making Surface Enhanced Pulp Fibers, Products Incorporating Surface Enhanced Pulp Fibers, and Methods of Making Products Incorporating Surface Enhanced Pulp Fibers, U.S. Appl. No. 61/692,880, filed Aug. 24, 2012.
Carvalho, et al., "A Comparative Study for Two Automated Techniques for Measuring Fiber Length," *Tappi Journal, Technical Association of The Pulp & Paper Industry*, 80(2): 137-142, 1997.
International Search Report and Written Opinion Issued in Corresponding PCT Patent Application No. PCT/US2020/025037, dated Jul. 16, 2020.

\* cited by examiner

PAPER PRODUCTS SUBJECTED TO A SURFACE TREATMENT COMPRISING ENZYME-TREATED SURFACE ENHANCED PULP FIBERS AND METHODS OF MAKING THE SAME

CROSS-REFERENCE WITH RELATED APPLICATIONS

This application claims priority to and the benefit of U.S. Provisional Application No. 62/824,113, filed Mar. 26, 2020, the contents of which are incorporated into the present application in its entirety.

FIELD OF INVENTION

The present invention relates generally to paper products subjected to a surface treatment and more particularly, but without limitation, to paper products that are sized using enzyme-treated pulp fibers.

BACKGROUND

For many paper products, such as coated base paper of printing and writing grades, it is desirable to have a smooth paper surface (e.g., of low porosity) that can resist the ingress of liquids into the paper. Paper is sometimes sized (e.g., subjected to a surface treatment) internally (e.g., at the stock preparation section) and/or externally (e.g., at the size press) using starch and, sometimes, fibrillated pulp fibers to seal the paper surface and thereby increase its resistance to liquids. Incorporating fibrillated pulp fibers as a sizing agent can reduce the amount of starch required to achieve desired surface characteristics, thereby reducing costs, and sizing that includes a comparatively large amount of fibrillated pulp fibers can yield a greater degree of sealing. However, increasing the amount of fibrillated pulp fibers in the sizing can increase the viscosity thereof. Compounds with relatively high viscosity may be unsuitable for use as sizing, at least because viscous compounds may be difficult to apply to a fibrous substrate and can form a non-uniform layer on the fibrous substrate, which can adversely affect paper quality and limit the amount of fibrillated pulp fibers that can be included in a sizing composition. Accordingly, there is a need in the art for methods of making a paper product that facilitate application of a surface sizing composition that comprises a plurality of fibrillated pulp fibers.

SUMMARY

The present methods address this need in the art at least by surface sizing a fibrous substrate with a furnish comprising enzyme-treated surface enhanced pulp fibers (SEPF). The SEPF can be highly fibrillated, e.g., can have a length weighted average fiber length that is greater than or equal to 0.20 millimeters and an average hydrodynamic specific surface area that is greater than or equal to 10 square meters per gram. Such highly fibrillated fibers can effectively fill holes in the surface of the fibrous substrate, yielding greater resistance to liquids and improving paper strength. Before the substrate is sized and after the SEPF are formed (e.g., by refining), one or more enzymes can be added to the furnish that comprises the SEPF. The enzyme(s) can modify the SEPF to reduce the viscosity of the furnish, which can facilitate uniform deposition of the furnish onto the fibrous substrate and permit larger proportions of SEPF to be used in the furnish. The enzyme(s) and treatment conditions can be selected such that reductions in the fiber length of the SEPF are mitigated during the enzyme treatment. Such surface treatments can yield a paper product with a greater resistance to liquids and improved printing characteristics, compared to conventional paper products.

Some methods of making a paper product comprise forming a substrate from a first furnish that comprises a plurality of pulp fibers, wherein optionally forming the substrate comprises depositing the first furnish onto a moving surface. In some methods, the pulp fibers of the first substrate comprise hardwood pulp fibers. Some methods comprise at least partially dewatering the substrate.

Some methods comprise treating a second furnish that comprises a plurality of surface enhanced pulp fibers (SEPF) at least by adding one or more enzymes to the second furnish. The SEPF, in some methods, are hardwood pulp fibers and, in other methods, are softwood pulp fibers. In some methods, the SEPF have a length weighted average fiber length that is greater than or equal to 0.20 millimeters (mm) and an average hydrodynamic specific surface area that is greater than or equal to 10 square meters per gram ($m^2/g$). In some methods, adding the enzyme(s) to the second furnish is performed such that the weight of the enzyme(s) in the furnish is between 0.005% and 10% of the weight of the SEPF in the second furnish. The enzyme(s), in some methods, comprise an endoglucanase, an exoglucanase (which, in some methods, is a cellobiohydralase) and, optionally, a mannanase. A viscosity of the treated second furnish, in some methods, is between 50 and 800 centipoise (e.g., as measured by viscometer at 100 RPM) (e.g., at a furnish consistency that is between 1% and 6% or 4%).

Some methods comprise sizing the dewatered substrate at least by depositing the treated second furnish onto at least one of opposing first and second surfaces of the dewatered substrate. Some methods comprise adding starch to the treated second furnish before depositing the treated second furnish, optionally such that, in the treated second furnish, the weight of the SEPF is between 10% and 90%, optionally between 40% and 60%, of the weight of the starch. In some methods, between 1% and 6%, by weight, of the treated second furnish is the SEPF when the treated second furnish is deposited. In some methods, dewatering the substrate is performed such that less than or equal to 40%, by weight, of the dewatered substrate is water when the treated second furnish is deposited. Depositing the treated second furnish, in some methods, is performed with a size press. In some methods, depositing the treated second furnish is performed such that, for each of the surface(s) of the dewatered substrate onto which the treated second furnish is deposited, the basis weight of the SEPF on the surface is between 0.2 and 3.0 grams per square meter (gsm).

Some methods comprise drying the sized substrate.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the terms "substantially" and "approximately" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, a product or system that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the products, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Figure 1:
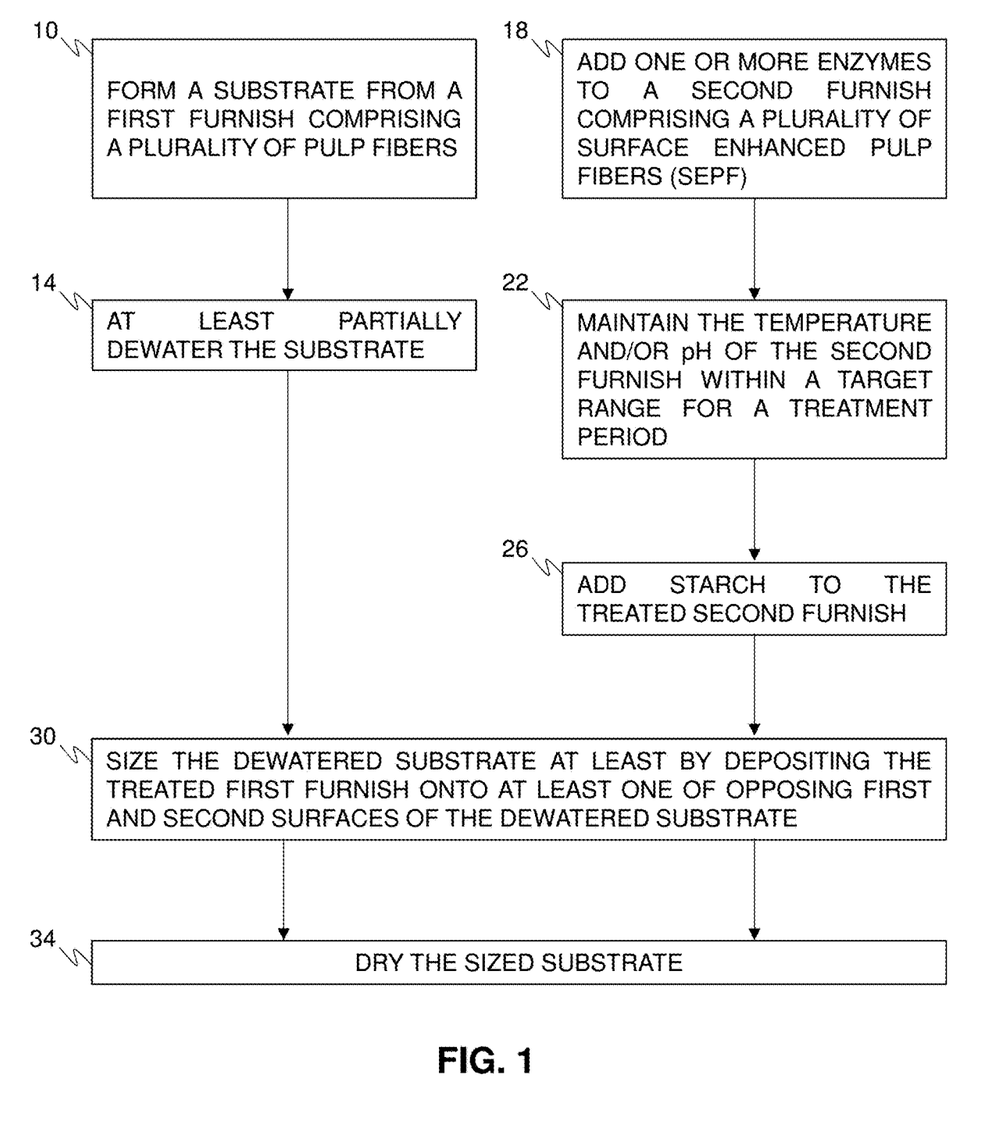
FIG. 1 illustrates one of the present methods of making a paper product in which a furnish comprising SEPF is treated with one or more enzymes and used to surface treat a substrate.
Figure 2A:
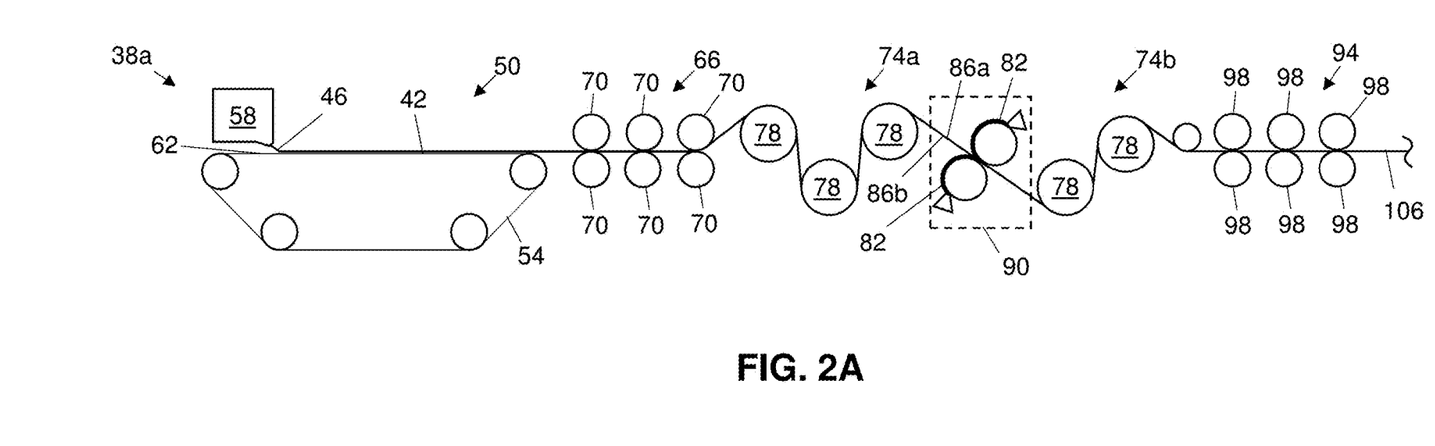
FIG. 2A is a schematic of a first system that can be used to form a paper product at least by externally sizing a substrate at a size press with a furnish that comprises enzyme-treated SEPF.

Referring to FIG. 1, shown are steps of some of the present methods of making a paper product, and referring to FIG. 2A, shown is a system 38a that can be used to perform at least some of the steps of FIG. 1. While some methods are described with reference to system 38a, system 38a is not limiting on those methods, which can be performed using any suitable system.

A paper product can be made from a fibrous substrate that has been internally and/or externally sized with a surface treatment that, as described in further detail below, can improve the strength, fluid resistance, and/or printing characteristics of the paper product. Some methods comprise a step 10 of forming the substrate (e.g., 42) from a first furnish (e.g., 46) that comprises a plurality of pulp fibers (e.g., that are suspended in water). The pulp fibers of the first furnish can comprise any suitable fibers, such as, for example, hardwood pulp fibers (e.g., originating from oak, gum, maple, poplar, eucalyptus, aspen, birch, and the like), softwood pulp fibers (e.g., originating from spruce, pine, fir, hemlock, southern pine, redwood, and the like), non-wood pulp fibers (e.g., originating kenaf, hemp, straws, bagasse, and the like), viscose fibers, or a combination thereof. Additionally or alternatively, the first furnish can comprise nanocrystalline cellulose. For some embodiments, at least some of the pulp fibers of the first furnish (e.g., greater than or equal to any one of, or between any two of, 1%, 2%, 3%, 4%, 5%, 6%, 7%, 8%, 9%, 10%, or more, by weight, of the pulp fibers) can be surface enhanced pulp fibers (SEPF), described in further detail below. The substrate can be formed at least by depositing the first furnish onto a permeable surface that can be moving. For example, system 38a can comprise a forming section (e.g., 50), which can include a forming fabric (e.g., 54) and a head box (e.g., 58) and, to form the substrate, the first furnish can be deposited onto a moving surface (e.g., 62) of the forming fabric using the head box. The basis weight of the pulp fibers in the substrate can be any suitable basis weight (e.g., depending on the desired paper product) such as, for example, greater than or equal to any one of, or between any two of, 10 grams per square meter (gsm), 50 gsm, 100 gsm, 150 gsm, 200 gsm, 250 gsm, 300 gsm, or more (e.g., between 30 and 75 gsm).

To facilitate sizing, some methods comprise a step 14 of at least partially dewatering the substrate. The substrate can be dewatered in any suitable manner, such as, for example, by draining, pressing, and/or drying the substrate. For example, system 38a can comprise a pressing section (e.g., 66) including one or more pressing elements (e.g., 70), each of which can be a roller, and one or more (e.g., two or more) drying sections (e.g., 74a and 74b), each of which can include one or more heated rollers (e.g., 78). The substrate can be drained on the moving surface of the forming fabric such that water from the substrate flows through the forming fabric (e.g., by gravity, by drawing water through the moving surface with one or more vacuums, and/or the like). Additionally or alternatively, the substrate can be pressed with the pressing element(s), and/or can be dried at least by passing the substrate partially around each of the heated roller(s) of a first one of the drying section(s) (e.g., 74a). The extent to which the substrate is dewatered before it is sized can depend at least in part on whether the substrate is to be sized internally or externally with the surface treatment. For example, as shown the substrate can be externally sized, e.g., less than or equal to any one of, or between any two of, 65%, 55%, 45%, 35%, 25%, 15%, 5%, or less (e.g., less than or equal to 40%) of the dewatered substrate, by weight, can be water when the surface treatment is applied (e.g., after the substrate is drained, pressed, and/or dried). However, as described in further detail below, in other embodiments the substrate can be internally sized, e.g., greater than or equal to any one of, or between any two of, 70%, 75%, 80%, 85%, 90%, or more of the dewatered substrate, by weight, can be water when the surface treatment is applied. As used herein, a "dewatered" substrate is a substrate from which at least some, optionally all or substantially all, of the water thereof has been removed.

The surface treatment can be made from a second furnish (e.g., 82) that comprises a plurality of SEPF (e.g., that are suspended in water). The SEPF can be hardwood pulp fibers, softwood pulp fibers, non-wood pulp fibers, or a combination thereof, and can be highly fibrillated. For example, the SEPF can have a length weighted average fiber length that is greater than or equal to any one of, or between any two of, 0.20 millimeters (mm), 0.30 mm, 0.40 mm, 0.50 mm, or larger (e.g., greater than or equal to 0.20 mm or 0.30 mm), and an average hydrodynamic specific surface area that is greater than or equal to any one of, or between any two of, 10 square meters per gram ($m^2/g$), 12 $m^2/g$, 14 $m^2/g$, 16 $m^2/g$, 18 $m^2/g$, 20 $m^2/g$, or larger (e.g., greater than or equal to 10 $m^2/g$). Optionally, the number of SEPF can be at least 12,000 per milligram on an oven-dry basis (e.g., based on a sample of the SEPF that is dried in an oven set at 105° C. for 24 hours). A description of SEPF and processes by which SEPF can be made are set forth in further detail in U.S. patent application Ser. No. 13/836,760, filed Mar. 15, 2013, and published as Pub. No. US 2014/0057105 on Feb. 27, 2014, which is hereby incorporated by reference. For example, some methods comprise making the SEPF at least by refining pulp fibers in one or more, optionally two or more, mechanical refiners such that the refiner(s) consume greater than or equal to any one of, or between any two of, 300 kilowatt-hours (kWh), 400 kWh, 300 kilowatt-hours (kWh), 400 kWh, 500 kWh, 600 kWh, 700 kWh, 800 kWh, 900 kWh, 1,000 kWh, or more (e.g., between 450 and 650 or between 350 and 500 kWh, for some hardwood pulp fibers, or at least 650 kWh or 1,000 kWh, for some softwood pulp fibers) per ton of fiber. Each of the refiner(s) can have a pair of refiner discs, each having relatively fine bar and groove widths such as a bar width that is less than or equal to any one of, or between any two of, 1.3 millimeters (mm), 1.2 mm, 1.1 mm, 1.0 mm, 0.9 mm, 0.8 mm, or less (e.g., less than or equal to 1.3 mm or 1.0 mm) and a groove width that is less than or equal to any one of, or between any two of, 2.5 mm, 2.3 mm, 2.1 mm, 1.9 mm, 1.7 mm, 1.5 mm 1.3 mm, or less (e.g., less than or equal to 2.5 mm, 1.6 mm, or 1.3 mm). In some embodiments, each of the refiner(s) can operate at a specific edge load that is less than or equal to any one of, or between any two of, 0.3 Watt-seconds per meter (W·s/m), 0.25 W·s/m, 0.20 W·s/m, 0.15 W·s/m, 0.10 W·s/m, or less (e.g., between 0.1 and 0.3 W·s/m or 0.1 and 0.2 W·s/m).

The high degree of fibrillation of the SEPF can facilitate bonding between the substrate and the SEPF and promote sealing of the paper product surface (e.g., by providing coverage of holes in the substrate to reduce the porosity thereof). Such sealing can impede liquids from penetrating the paper product and promote desirable printing characteristics and strength. The second furnish can have any suitable consistency for depositing the second furnish onto the dewatered substrate; for example, less than or equal to any one of, or between any two of, 10%, 9%, 8%, 7%, 6%, 5%, 4%, 3%, 2%, 1%, or less (e.g., between 1% and 6%) of the second furnish, by weight, can be the SEPF. Increasing the proportion of SEPF in the second furnish may promote sealing.

Some methods comprise treating the second furnish to facilitate deposition of the second furnish onto the dewatered substrate. The second furnish can be treated at least by performing a step 18 of adding one or more enzymes to the second furnish (e.g., after the SEPF are produced by refining). The enzyme(s) can modify the SEPF to reduce the viscosity of the second furnish, which can facilitate uniform deposition of the second furnish onto the dewatered substrate and thereby promote paper quality. The enzyme(s) can include any suitable enzyme(s), such as, for example, an endoglucanase, an exoglucanase (e.g., a cellobiohydrolase), a mannanase, and/or a xylanase. The combination of an endoglucanase and an exoglucanase (e.g., a cellobiohydralase) can be particularly suitable for modifying the SEPF; the addition of those enzymes to the second furnish may achieve greater reductions in the viscosity of the second furnish with smaller reductions in the fiber length of the SEPF, compared to other enzymes. Treatment with an endoglucanase and an exoglucanase may accordingly better facilitate application of the treated second furnish to the dewatered substrate (e.g., to yield greater uniformity and more sealing) than other enzymes. When the SEPF in the second furnish are softwood pulp fibers, the addition of a mannanase can further facilitate the surface treatment. Adding the enzyme(s) to the second furnish can be performed such that the second furnish comprises any suitable proportion of enzyme(s), e.g., such that the weight of the enzyme(s) in the second furnish is greater than or equal to any one of, or between any two of, 0.005%, 0.05%, 0.50%, 1%, 2%, 3%, 4%, 5%, 6%, 7%, 8%, 9%, 10%, or more (e.g., between 0.005% and 10%) of the weight (e.g., the dry weight) of the SEPF in the second furnish.

After the enzyme(s) are added to the second furnish, and to achieve a desired level of SEPF modification for deposition of the second furnish onto the dewatered substrate, the second furnish can be maintained at conditions that facilitate enzyme activity for a treatment period. For example, some methods comprise a step 22 of maintaining the temperature and/or pH of the second furnish within a target range for the treatment period. To illustrate, treating the second furnish can be performed such that, after the enzyme(s) are added to the second furnish and for the treatment period, the temperature of the second furnish is greater than or equal to any one of, or between any two of, 20° C., 25° C., 30° C., 35° C., 40° C., 45° C., 50° C., 55° C., 60° C., 65° C., 70° C., or higher (e.g., between approximately 40° C. and 65° C. or between 30° C. and 55° C.), and/or the pH of the second furnish is greater than or equal to any one of, or between any two of, 2.5, 3.0, 3.5, 4.0, 4.5, 5.0, 5.5, 6.0, 6.5, 7.0, 7.5, 8.0, or higher (e.g., between approximately 3.5 and 7.0). The treatment period can be of any suitable length, such as, for example greater than or equal to any one of, or between any two of, 30 minutes, 1 hour, 2 hours, 3 hours, 4 hours, 5 hours, 6 hours, 7 hours, 8 hours, 9 hours, 10 hours, or more (e.g., between 30 minutes and 10 hours or between 3 hours and 6 hours).

Treating the second furnish with the enzyme(s) can significantly reduce the viscosity of the second furnish. For example, depending at least in part on the proportion of SEPF in the second furnish, a viscosity of the second furnish before the addition of the enzyme(s) may be greater than 1,800 centipoise (cP) (e.g., greater than 4,500 cP), and a viscosity of the treated second furnish can be less than or equal to any one of, or between any two of, 1,000 cP, 900 cP, 800 cP, 700 cP, 600 cP, 500 cP, 400 cP, 300 cP, 200 cP, 100 cP, 50 cP, or less (e.g., between 50 and 800 cP). As used herein, viscosity can be measured by a viscometer (e.g., a viscometer available from Brookfield) at 100 RPM. The second furnish can have such viscosities at furnish consistencies (e.g., the mass of solids as a percent of the mass of the furnish) that are, for example, less than or equal to any one of, or between any two of, 6%, 5%, 4%, 3%, 2%, 1%, or less (e.g., between 1% and 6% or 4%). Such a reduction in viscosity can facilitate deposition of the treated second furnish onto the dewatered substrate.

Before the treated second furnish is deposited onto the dewatered substrate, some methods comprise a step 26 of adding starch (e.g., an ethylated starch) to the treated second furnish. When incorporated into the surface treatment, the starch, in conjunction with the SEPF, can promote paper strength and facilitate sealing of the surface of the paper product. Any suitable proportion of starch, relative to the SEPF, can be added to the treated second furnish. For example, the starch can be added to the treated second furnish such that the weight of the SEPF in the treated second furnish is less than or equal to any one of, or between any two of, 90%, 80%, 70%, 60%, 50%, 40%, 30%, 20%, 10%, or less (e.g., between 20% and 70%, such as between 20% and 40%, 40% and 60%, or 50% and 70%) of the weight of the starch in the treated second furnish. Such relative proportions of SEPF and starch in the treated second furnish (e.g., a SEPF weight of between 20% and 70%, such as between 20% and 40%, 40% and 60%, or 50% and 70% of the starch weight) can promote the runnability of the treated second furnish and thereby facilitate the deposition thereof onto the dewatered substrate. After the starch is added, the viscosity of the treated second furnish with starch can be less than or equal to any one of, or between any two of, 1,000 cP, 900 cP, 800 cP, 700 cP, 600 cP, 500 cP, 400 cP, 300 cP, 200 cP, 100 cP, 50 cP, or less (e.g., between 50 and 700 cP, such as between 50 and 300 cP).

After the second furnish is treated, some methods comprise a step 30 of sizing (e.g., applying a surface treatment to) the dewatered substrate at least by depositing the treated second furnish onto at least one of opposing first and second surfaces (e.g., 86a and 86b) of the dewatered substrate. For each of the surface(s) of the dewatered substrate onto which the treated second furnish is deposited, the treated second furnish can form a layer (e.g., comprising the SEPF and, optionally, starch), optionally in which the basis weight of SEPF is greater than or equal to or between any two of 0.2 gsm, 0.5 gsm 1.0 gsm, 1.5 gsm, 2.0 gsm, 3.0 gsm, 3.5 gsm, or greater (e.g., between 1 and 3 gsm). The treated second furnish can be deposited in any suitable manner; as shown, the treated second furnish is deposited with a size press (e.g., 90) (e.g., a pond size press or a rod-metering size press). To illustrate, when the size press is a rod-metering size press, it can comprise two transfer rollers between which the dewatered substrate is passed. The second furnish can be deposited onto each of the transfer rollers by directing the second furnish between the transfer roller and a rod that can have a smooth surface or a surface that defines a plurality of grooves. The second furnish deposited onto each of the transfer rollers can be transferred onto the surfaces of the dewatered substrate as it passes therebetween. In other embodiments, however, the treated second furnish can be deposited using any suitable apparatus, such as, for example, with a blade coater, a fountain coater, a cascade coater, a spray applicator, a head box, or the like. Before the second furnish is deposited, it can be passed through a screen (e.g., having a mesh number that is greater than or equal to any one of, or between any two of, 70, 80, 100, 120, or 140).

To form the paper product, some methods comprise a step 34 of drying the sized substrate, e.g., at least by passing the sized substrate partially around each of the heated roller(s) of a second one of the drying sections (e.g., 74b). And, optionally, the sized substrate can be subjected to one or more additional processing steps to achieve desired paper characteristics. For example, the sized substrate can be coated and/or can be pressed after the sized substrate is dried (e.g., for each of one or more pairs of calender rolls (e.g., 98) in a calendering section (e.g., 94) of system 38a, by passing the sized substrate between the calender rolls).

Figure 2B:
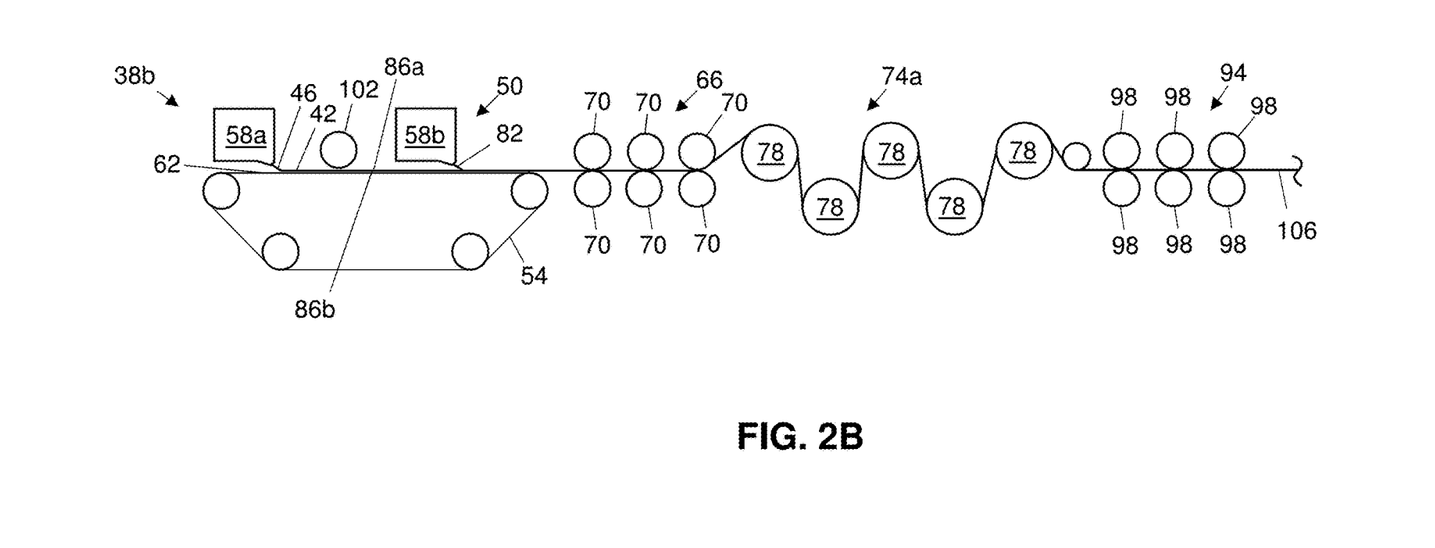
FIG. 2B is a schematic of a second system that is substantially the same as the system of FIG. 2A, the primary exception being that the second system is configured to internally size the substrate with a furnish that comprises enzyme-treated SEPF using a second head box.

While as shown the dewatered substrate is externally sized (e.g., less than or equal to 40%, by weight, of the dewatered substrate is water when the treated second furnish is deposited), in other embodiments the dewatered substrate can be internally sized (e.g., greater than or equal to 70%, such as at least 95%, of the dewatered substrate can be water by weight when the treated second furnish is deposited). Referring to FIG. 2B, shown is a system 38b that is substantially similar to system 38a, the primary exception being that system 38b is configured to deposit the treated second furnish onto the dewatered substrate at the wet-end of the system to internally size the dewatered substrate. For example, system 38b can comprise a first head box (e.g., 58a) and a second head box (e.g., 58b) disposed downstream of the first head box. The substrate can be formed at least by depositing the first furnish onto the moving surface with the first head box. The dewatered substrate can be sized at least by depositing the treated second furnish onto the dewatered substrate with the second head box (e.g., while the dewatered substrate is disposed on the moving surface). To facilitate dewatering of the substrate, system 38b can include a roller (e.g., 102) positioned between the first and second head boxes; the substrate can be dewatered at least by pressing the substrate with the roller (e.g., while the substrate is disposed on the moving surface). The sized substrate can thereafter be pressed (e.g., with the pressing element(s) of the pressing section), dried (e.g., by passing the sized substrate partially around each of the heated rollers of the drying section), and/or calendered.

In some methods, the dewatered substrate can be both internally and externally sized. For such methods, at least one, optionally both, of the internal and external sizing can be the treated second furnish. For example, the substrate can be internally sized with a solution comprising starch (e.g., the solution can be deposited onto the dewatered substrate when greater than or equal to 70%, such as at least 95%, of the dewatered substrate is water by weight) and thereafter externally sized using the treated second furnish as described above (e.g., such that the dewatered substrate comprises starch when the treated second furnish is deposited onto the dewatered substrate). However, in other methods any suitable combination of internal and external sizing can be applied to the dewatered substrate.

Figure 3:
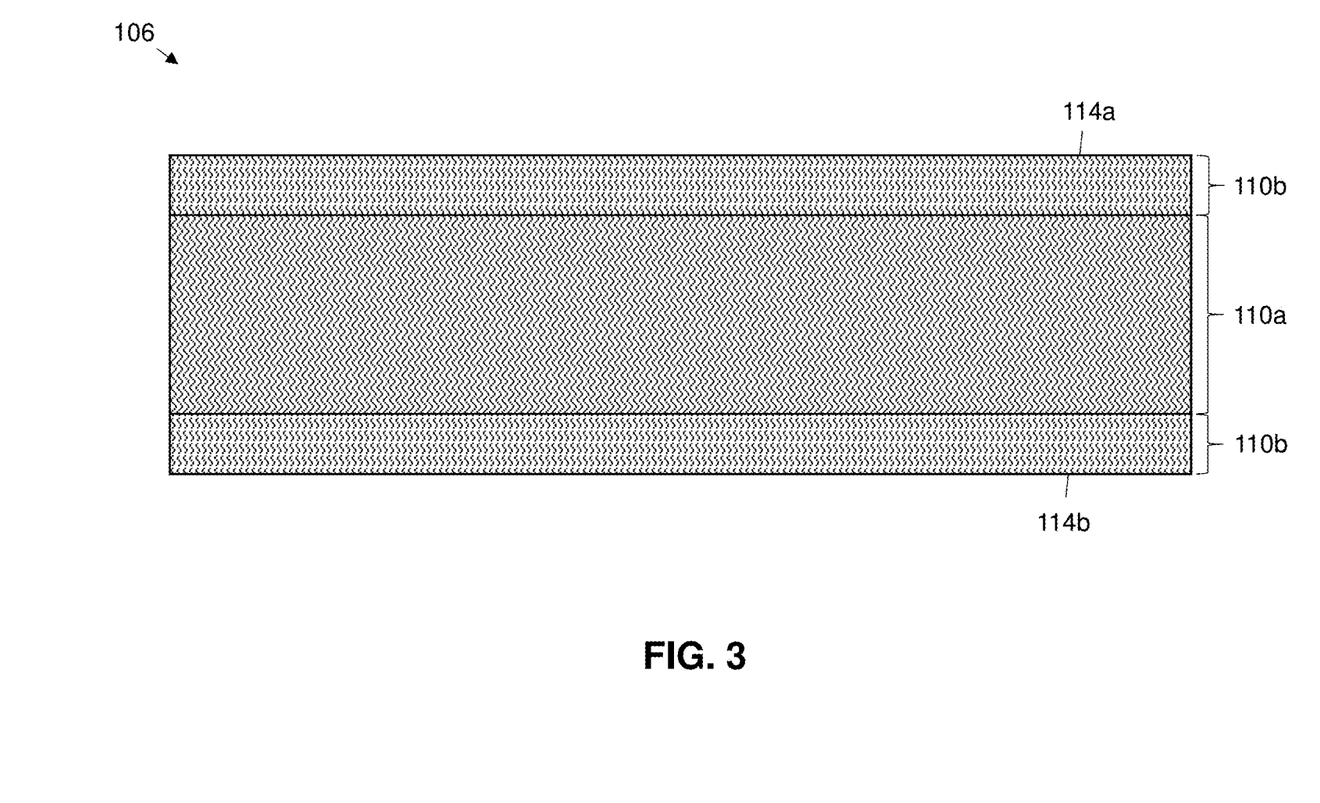
FIG. 3 is a schematic cross-section of a paper product made according to some of the present methods.

Referring to FIG. 3, a paper product 106 formed according to some of the present methods can comprise one or more first fiber regions 110a and one or more (e.g., two or more) second fiber regions 110b, each comprising a plurality of pulp fibers (e.g., any of those described above). Each of second fiber region(s) 110b can define one of opposing top and bottom surfaces 114a and 114b of paper product 106 and at least 90% of the pulp fibers of each of the second fiber region(s) can be the enzyme-treated SEPF (e.g., with any of the above-described basis weights). Optionally, each of second fiber region(s) 110b can comprise starch in any suitable proportion relative to the SEPF thereof (e.g., any of the proportions described above). Each of second fiber region(s) 110b can be disposed on at least one of first fiber region(s) 110a. The pulp fibers of each of first fiber region(s) 110a can comprise a smaller proportion of SEPF than second fiber region(s) 110b (e.g., at least 80% or 90% of the pulp fibers of each of the first fiber region(s) can have a length weighted average fiber length and/or average hydrodynamic specific surface area that are less than those of the SEPF in each of the second fiber region(s)).

EXAMPLES

The present invention will be described in greater detail by way of specific examples. The following examples are offered for illustrative purposes only and are not intended to limit the present invention in any manner. Those skilled in the art will readily recognize a variety of non-critical parameters that can be changed or modified to yield essentially the same results.

Example 1

Figure 4A:
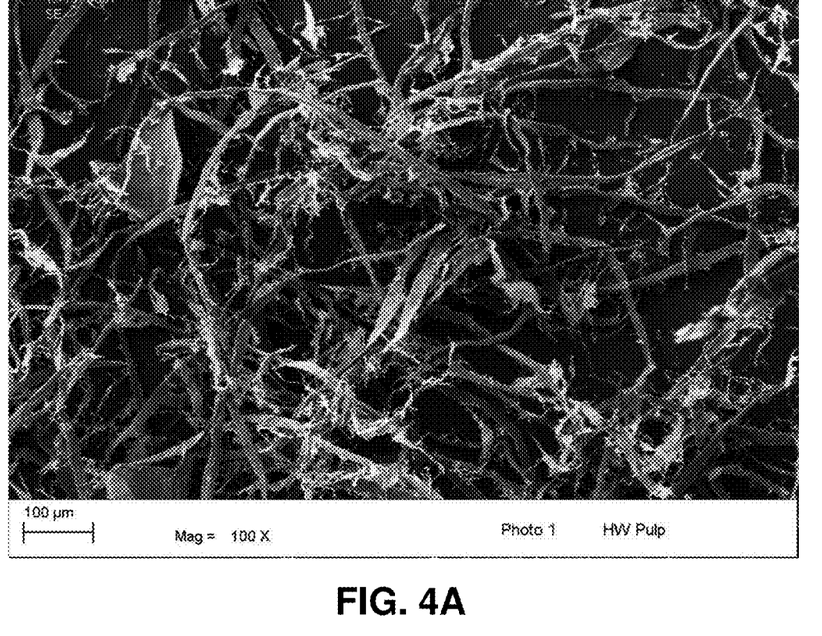
FIG. 4A is an image of unrefined Northern mixed hardwood pulp fibers.
Figure 4B:
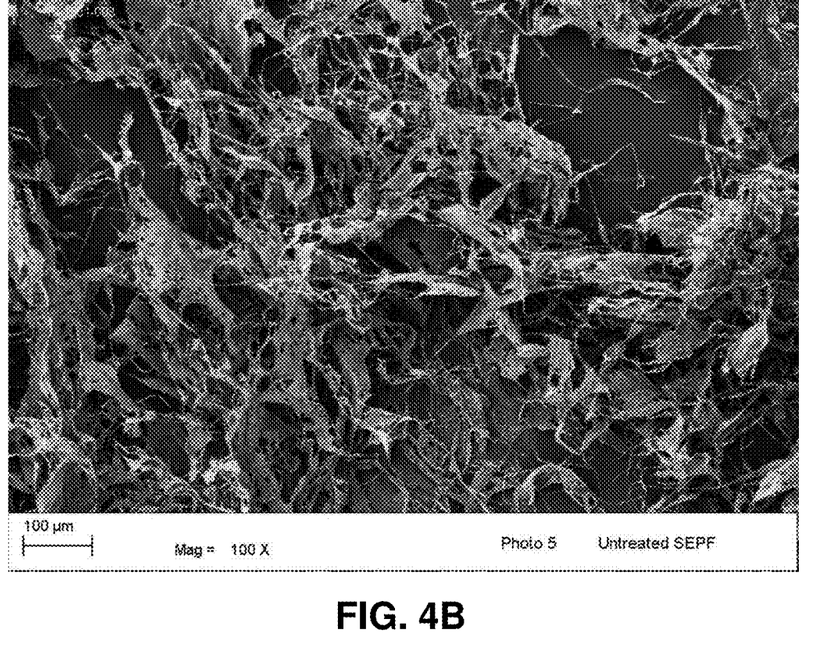
FIG. 4B is an image of SEPF produced by refining the pulp fibers of FIG. 4A.
Figure 4C:
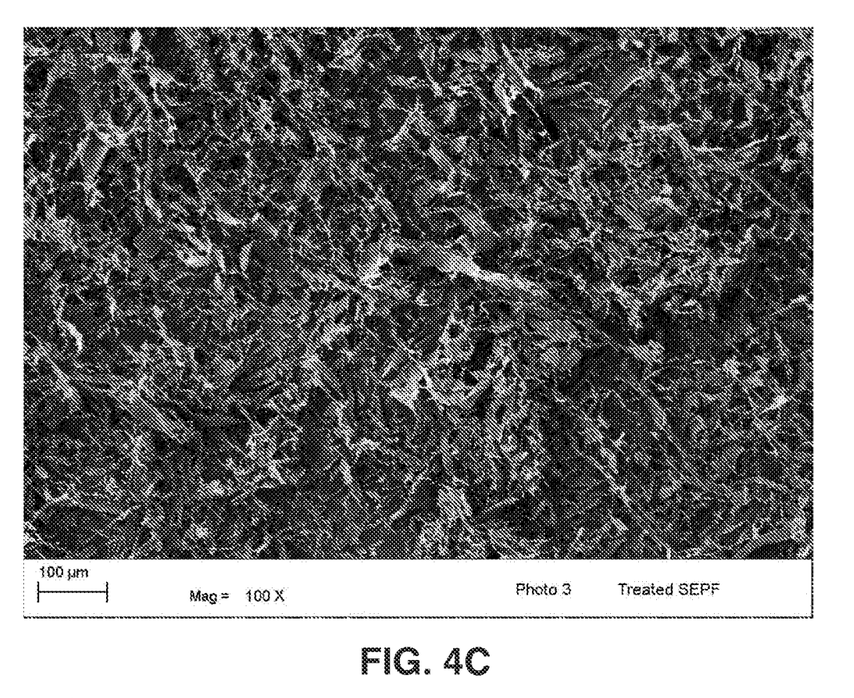
FIG. 4C is an image of the SEPF of FIG. 4B after the SEPF were modified with an endoglucanase and an exoglucanase.

Referring to FIGS. 4A-4C, a plurality of unrefined Northern mixed hardwood pulp fibers (FIG. 4A) were refined to produce SEPF (FIG. 4B). The produced SEPF were highly fibrillated and exhibited a large increase in average hydrodynamic specific surface area, compared to the unrefined pulp fibers. An endoglucanase and an exoglucanase (a cellobiohydralase) were added to the SEPF, which modified the SEPF (FIG. 4C).

Example 2

In two trials, SEPF-containing furnishes were treated with an endoglucanase and an exoglucanase (a cellobiohydralase) at different treatment conditions. For each, the SEPF were formed from Northern mixed hardwood pulp fibers.

In the first trial, four different doses of enzymes were added to a furnish having a SEPF consistency of 2.5% (e.g., 2.5%, by weight, of the furnish was SEPF)—the enzyme doses were 10%, 5%, 2.5%, and 0.5% (e.g., the enzymes were added such that the weight of the enzymes was 10%, 5%, 2.5%, and 0.5% of the weight of the SEPF in the furnish). The furnish was maintained at a temperature of approximately 50° C. and a pH of between approximately 6 and 7 for 4-5 hours. The viscosity of the untreated furnish was 1,900 centipoise and, for each of the doses, decreased to 300-400 centipoise.

In the second trial, the furnish had a SEPF consistency of 4% (e.g., 4%, by weight, of the furnish was SEPF) and the enzymes were added to the furnish such that the weight of the enzymes was 5% of the SEPF in the furnish. The furnish was maintained at a temperature of approximately 50° C. and a pH of approximately 7 for 4-5 hours. The viscosity of the furnish decreased from 4,600 centipoise to 600 centipoise after the treatment.

Example 3

Five trials were performed in which a furnish was applied to both sides of a paper substrate using a VALMET® OptiSizer Film Coater: a control in which the furnish comprised starch without pulp fibers and four trials in which the furnish comprised starch and SEPF treated with endoglucanase and exoglucanase. For all trials, the starch was hydroxyethylated dent corn starch (ETHYLEX® 2020). In each of the trials the furnish was metered onto transfer rollers of the OptiSizer Film Coater to form a film on the rollers, which was transferred to the paper substrate as the substrate passed through the nip between the rollers. For each of the transfer rollers of the OptiSizer Film coater, a rod metered the furnish supplied to the transfer roller to control the weight of the film deposited thereon. TABLE 1 sets forth the properties of the paper substrate before being coated by the furnish.

TABLE 1

| Untreated Base Paper Properties | |
| --- | --- |
| Grammage (g/m$^2$) | 61 |
| Moisture Content (wt. %) | 5.31 |
| Parker Print-Surf (PPS) roughness (S10)—Top (μm) | 4.01 |
| PPS S10—Bottom (μm) | 4.36 |
| Bendtsen Air Porosity (mL/min) | 467.67 |
| Gurley Air Resistance (s) | 24.00 |
| Cobb Oil Absorption—6 s—Top (g/m$^2$) | 17.06 |
| Cobb Oil Absorption—6 s—Bottom (g/m$^2$) | 18.23 |
| Cobb Water Absorption—30 s—Top (g/m$^2$) | 14.4 |
| Cobb Water Absorption—30 s—Bottom (g/m$^2$) | 14.1 |
| Opacity—C/2°—Top (g/m$^2$) | 82.81 |
| Opacity—C/2°—Bottom (g/m$^2$) | 82.77 |

For each of the non-control trials, the furnish was made by introducing the SEPF and starch in a pigment mixer in which they were pre-heated to a temperature that was 55-60° C. and mixed. Before being mixed with the starch, the SEPF-containing pulp had viscosity of 279 cP and 3.36% of the pulp was solids.

Figure 5A:
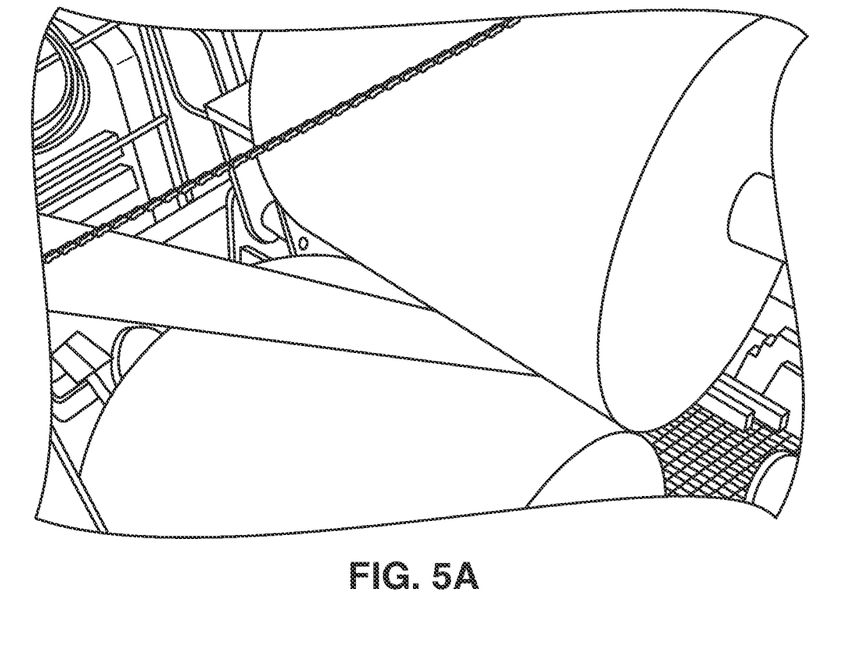
FIGS. 5A-5C are images of VALMET® OptiSizer Film Coater applying some of the present SEPF-containing furnishes to the top and bottom surfaces of a paper substrate.
Figure 5B:
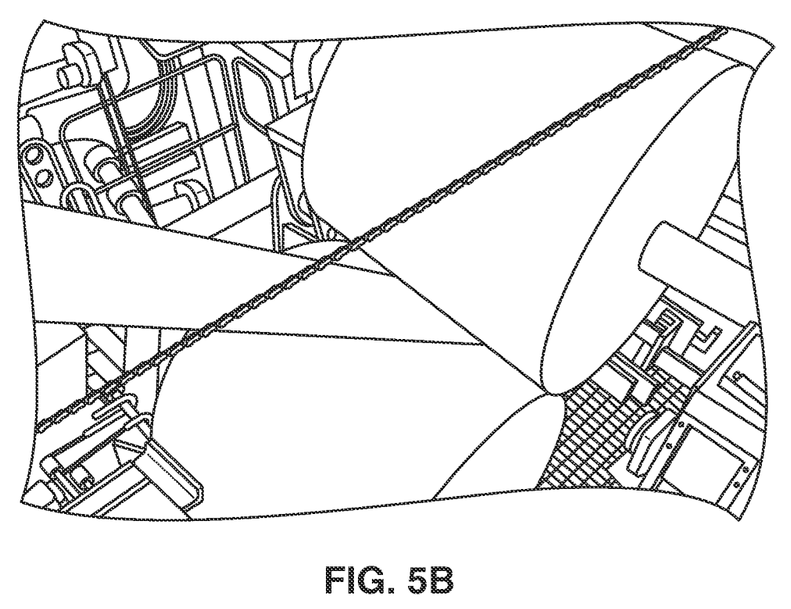
Figure 5C:
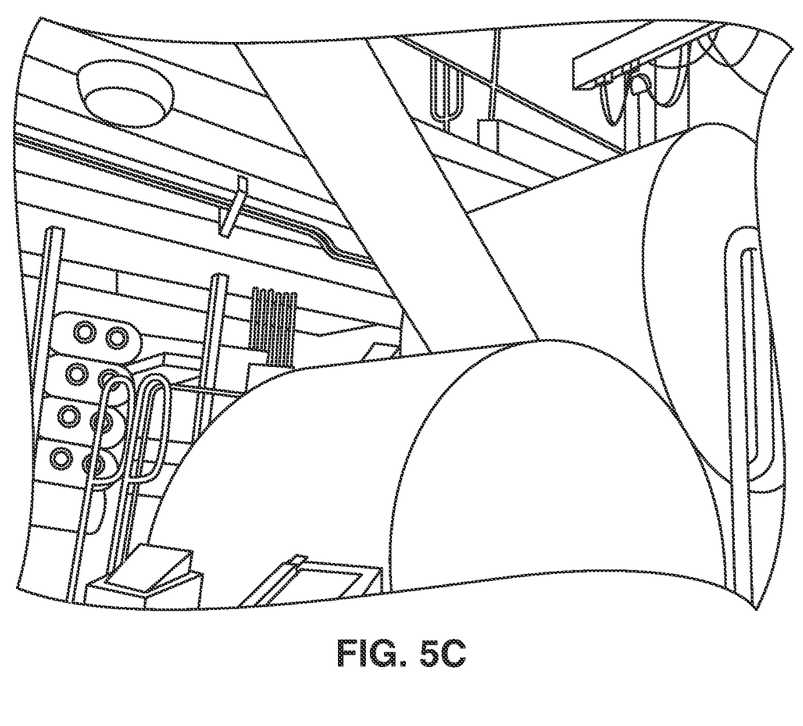

For all trials, the nip load of the OptiSizer Film Coater was 25 kN/m and the paper substrate was run at a rate of 600 m/min. Among the trials, the rods were adjusted to achieve different film and resulting coating weights on the paper substrate. The rods used were grooved to facilitate film formation for these particular conditions; in a prior trial in which the ratio of Starch:SEPF weight was 5:3, using smooth rods did not yield a film on the transfer rollers under the particular conditions tested, although smooth rods were expected to form a film under different conditions. Different relative weights of SEPF and starch were used for the non-control trials. FIGS. 5A-5C illustrate the OptiSizer Film Coater applying a furnish to the paper substrate in the first, second, and third non-control trials, respectively. TABLE 2 sets forth, for each of the trials, the basis weight of the coating that was deposited on each side of the paper substrate, the wet film basis weight applied to the transfer rollers, the percent of the furnish comprising solids by weight, and the viscosity, temperature, and pH of the furnish. For each of the non-control trials, TABLE 2 also sets forth the ratio of starch to SEPF, by weight, in the furnish.

TABLE 2

| Trial Coating Parameters | | | | | |
| --- | --- | --- | --- | --- | --- |
| Trial | Control | 1 | 2 | 3 | 4 |
| Starch: SEPF Ratio | — | 5:3 | 5:3 | 3:1 | 3:1 |
| Coat Weight (g/m$^2$) | 2 | 1.9 | 1.7 | 1.3 | 1.5 |
| Wet Film (g/m$^2$) | 18 | 25 | 23 | 17 | 20 |
| Furnish Solids (wt. %) | 12.4 | 8.3 | 7.8 | 8.4 | 8.4 |
| Viscosity (cP) | 42 | 417 | 630 | 240 | 240 |
| Temperature (° C.) | 61 | 60 | 58 | 60 | 60 |
| pH | 8.0 | 6.9 | 7.8 | 7.9 | 7.9 |

In the control, the furnish formed a good film on the transfer roller. For each of Trials 1 and 2, the furnish formed a good film on the transfer rollers but a mini pond formed, resulting in some splashing from the nip, with the substrate in Trial 1 not accepting all of the film (FIGS. 5A and 5B). For each of Trials 3 and 4, in which the furnish had a lower viscosity than those in Trials 1 and 3 due to lower amount of SEPF in the furnish, the furnish formed a good film on the transfers rollers and there was no mini pond or splashing (FIG. 5C, showing Trial 3).

The properties of the coated paper were measured in each of the trials, which are set forth in TABLE 3. FIGS. 6A-6F illustrate the resulting PPS, Bendtsen Air Porosity, Gurley Air Resistance, Cobb Oil Absorption (6 s), Cobb Water Absorption (30 s), and Opacity)(C/2°, respectively, of the substrate and all coating trials.

TABLE 3

Measurements of Coated Paper Surface Properties

| Trial | Control | 1 | 2 | 3 | 4 |
|---|---|---|---|---|---|
| Moisture Content (wt. %) | 5.38 | 6.55 | 5.72 | 5.06 | 4.49 |
| PPS S10—Top (µm) | 5.50 | 5.49 | 5.61 | 5.22 | 5.38 |
| PPS S10—Bottom (µm) | 6.13 | 6.20 | 6.22 | 6.12 | 6.07 |
| Bendtsen Air Porosity (mL/min) | 288.33 | 116.17 | 110.67 | 150.00 | 138.17 |
| Gurley Air Resistance (s) | 38.95 | 96.28 | 101.55 | 74.82 | 81.67 |
| Cobb Oil Absorption—6 s—Top (g/m$^2$) | 10.85 | 7.26 | 6.94 | 8.75 | 8.36 |
| Cobb Oil Absorption—6 s—Bottom (g/m$^2$) | 10.91 | 7.82 | 7.40 | 9.73 | 9.08 |
| Cobb Water Absorption—30 s—Top (g/m$^2$) | 52.3 | 60.5 | 60.0 | 49.9 | 47.5 |
| Cobb Water Absorption—30 s—Bottom (g/m$^2$) | 51.9 | 62.5 | 59.4 | 51.4 | 47.4 |
| Opacity—C/2°—Top (g/m$^2$) | 80.09 | 82.68 | 82.11 | 81.96 | 81.38 |
| Opacity—C/2°—Bottom (g/m$^2$) | 80.33 | 82.31 | 81.58 | 81.21 | 81.54 |

Figure 6A:
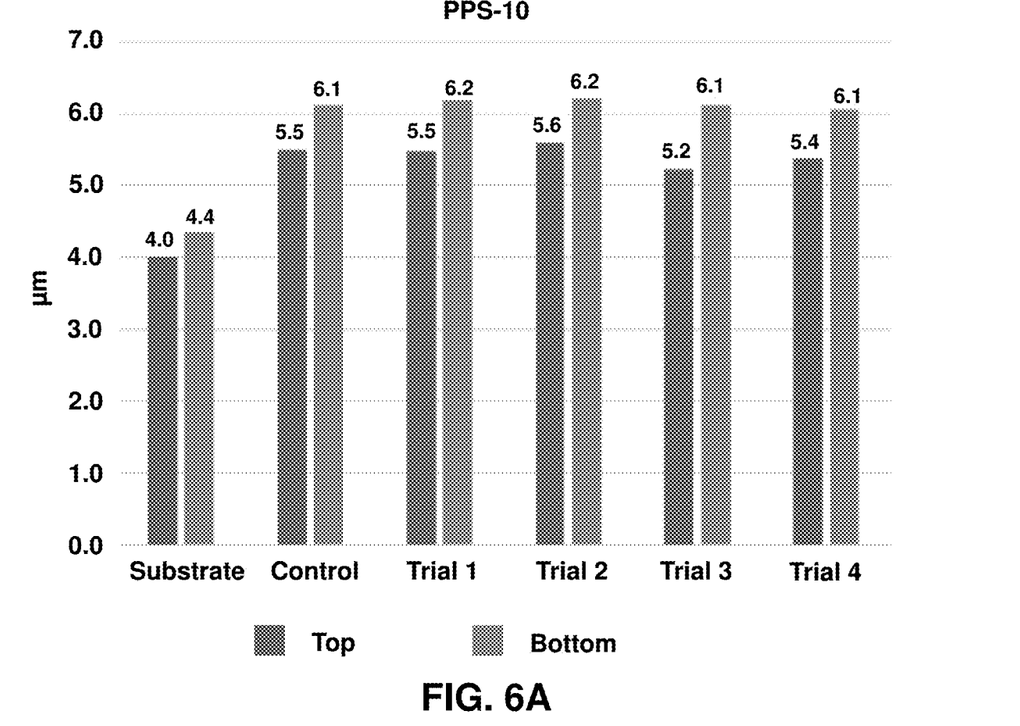
FIGS. 6A-6F are graphs illustrating the Parker Print-Surf (PPS) roughness, Gurley Air Resistance, Cobb Oil Absorption, Cobb Water Absorption, and Opacity, respectively, of an uncoated paper substrate, a paper coated with starch alone, and four papers coated with some of the present SEPF-containing furnishes.
Figure 6B:
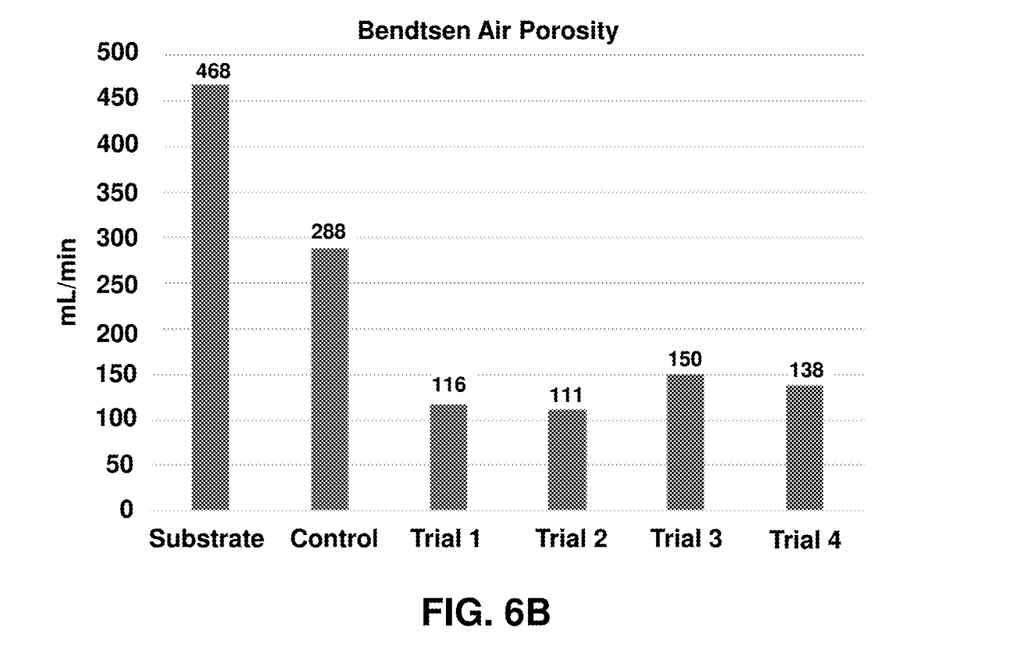
Figure 6C:
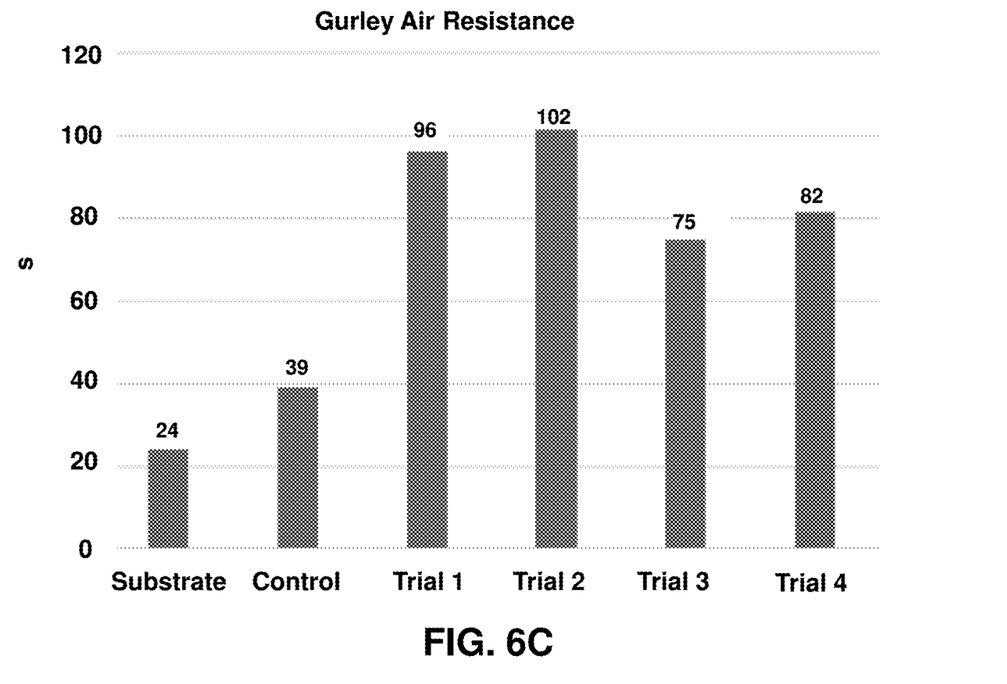
Figure 6D:
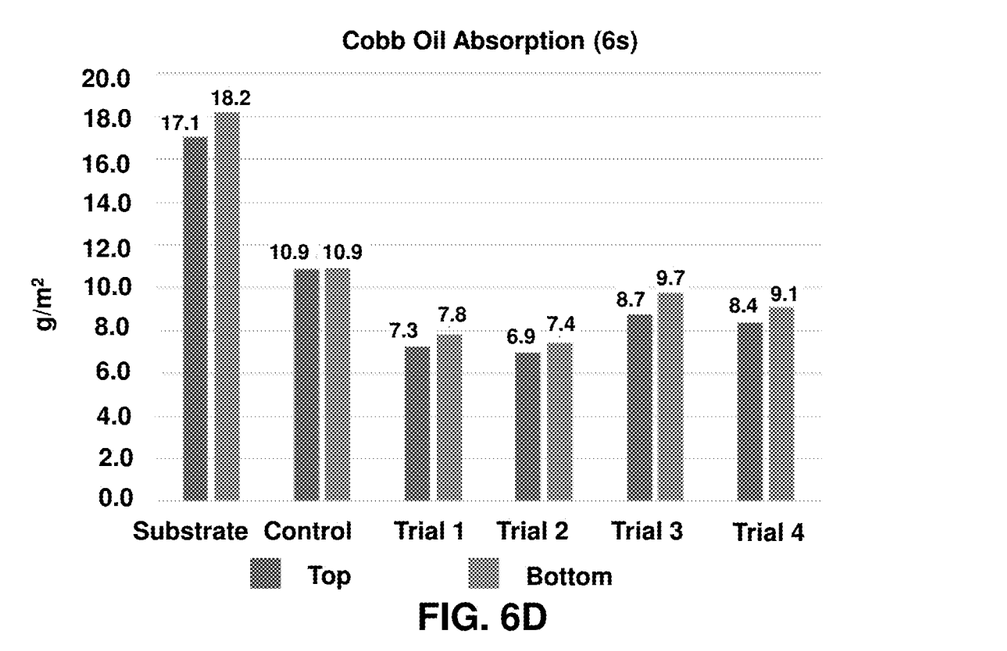
Figure 6E:
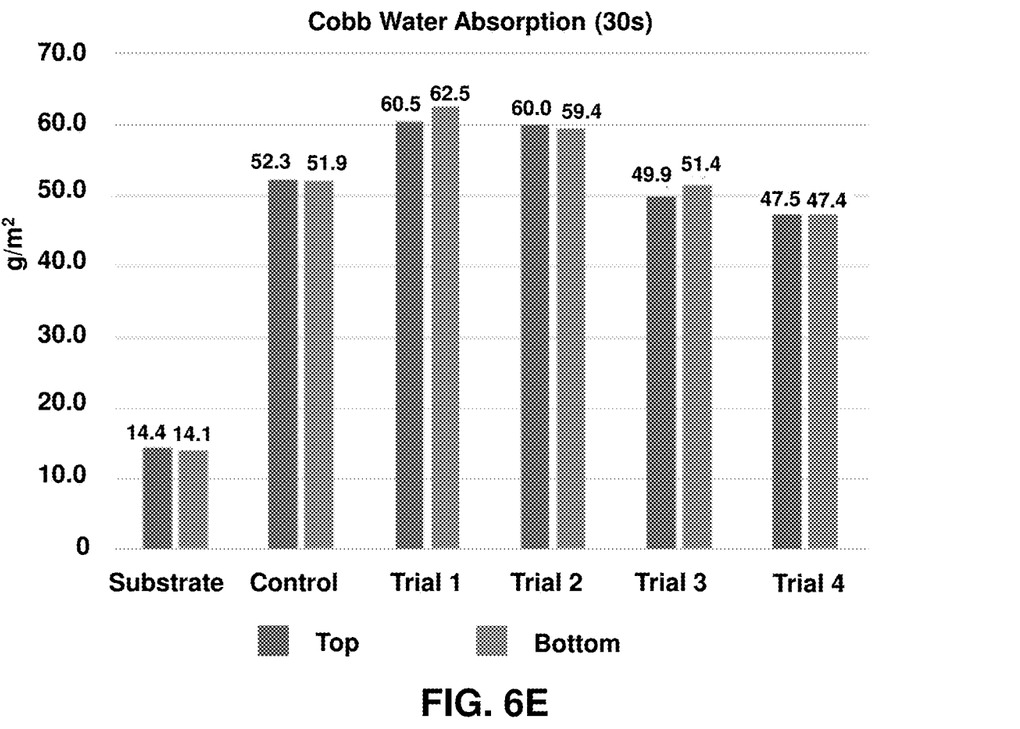
Figure 6F:
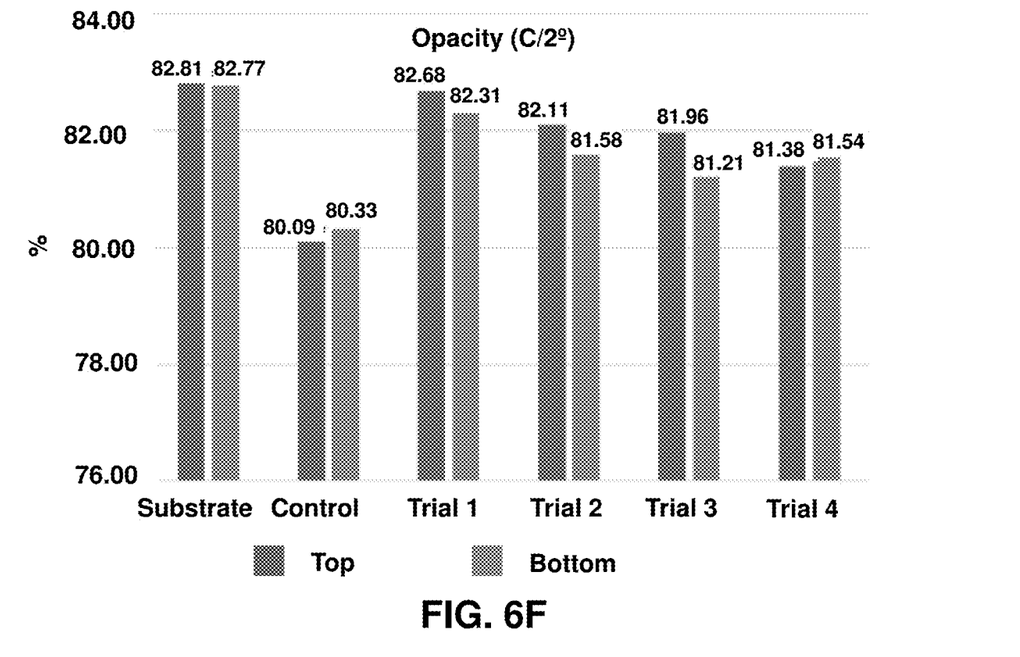

All of the trial coatings had a similar effect on PPS porosity (FIG. 6A) and yielded a lower Bendtsen Air Porosity, relative to the substrate (FIG. 6B). The SEPF-containing furnishes produced lower air porosities than the starch-only furnish, with the furnishes having a 5:3 ratio of starch:SEPF yielding a lower air porosity than the furnishes having a 3:1 ratio of starch:SEPF. The SEPF-containing furnishes significantly increased the Gurley Air Resistance of the substrate, compared to the starch-only furnish, with the furnishes having a 5:3 ratio of starch:SEPF yielding a slightly larger air resistance than the furnishes having a 3:1 ratio (FIG. 6C). All coatings decreased Cobb Oil Absorption, with the SEPF-containing furnishes decreasing it more so than the starch-only furnish and the 5:3 starch:SEPF ratio furnish decreasing it more so than the 3:1 starch:SEPF ratio furnish (FIG. 6D). All of the coatings increased Cobb Water Absorption such that all coated papers were broken down due to water penetration, with only the uncoated paper substrate remaining intact (FIG. 6E). The coatings did not increase the opacity of the paper substrate (FIG. 6F).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the products, systems, and methods are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of making a paper product, the method comprising:
    forming a substrate from a first furnish that comprises a plurality of pulp fibers;
    at least partially dewatering the substrate;
    treating a second furnish that comprises a plurality of surface enhanced pulp fibers (SEPF) at least by adding one or more enzymes to the second furnish, the SEPF having a length weighted average fiber length that is greater than or equal to 0.20 millimeters (mm) and an average hydrodynamic specific surface area that is greater than or equal to 10 square meters per gram (m2/g), the one or more enzymes being configured to reduce a viscosity of the second furnish;
    sizing the dewatered substrate at least by depositing the treated second furnish onto at least one of opposing first and second surfaces of the dewatered substrate; and
    drying the sized substrate.

2. The method of claim 1, comprising adding starch to the treated second furnish before depositing the treated second furnish.

3. The method of claim 2, wherein adding starch to the treated second furnish is performed such that, in the treated second furnish, the weight of the SEPF is between 10% and 90% of the weight of the starch.

4. The method of claim 3, wherein adding starch to the treated second furnish is performed such that, in the treated second furnish, the weight of the SEPF is between 40% and 60% of the weight of the starch.

5. The method of claim 1, wherein adding the enzyme(s) to the second furnish is performed such that the weight of the enzyme(s) in the second furnish is between 0.005% and 10% of the weight of the SEPF in the second furnish.

6. The method of claim 1, wherein the enzyme(s) comprise an endoglucanase and an exoglucanase.

7. The method of claim 6, wherein the exoglucanase is a cellobiohydralase.

8. The method of claim 1, wherein dewatering the substrate is performed such that less than or equal to 40%, by weight, of the dewatered substrate is water when the treated second furnish is deposited.

9. The method of claim 1, wherein depositing the treated second furnish is performed with a size press.

10. The method of claim 1, wherein between 1% and 6%, by weight, of the treated second furnish is the SEPF when the treated second furnish is deposited.

11. The method of claim 1, wherein about 4%, by weight, of the treated second furnish is the SEPF when the treated second furnish is deposited.

12. The method of claim 1, wherein depositing the treated second furnish is performed such that, for each of the surface(s) of the dewatered substrate onto which the treated second furnish is deposited, the basis weight of the SEPF on the surface is between 0.2 and 3.0 grams per square meter (gsm).

13. The method of claim 1, wherein forming the substrate comprises depositing the first furnish onto a moving surface.

14. The method of claim 1, wherein: the pulp fibers of the first furnish comprise hardwood pulp fibers; and the SEPF are hardwood pulp fibers.

15. The method of claim 1, wherein the one or more enzymes have between 0.005 percent and 10 percent of a weight of the SEPF in the second furnish.

16. The method of claim 1, wherein sizing the dewatered substrate is performed by depositing the treated second furnish onto the opposing first and second surfaces of the dewatered substrate.

17. The method of claim 1, wherein the first furnish and the second furnish are different.

* * * * *